(12) United States Patent
Barrett et al.

(10) Patent No.: US 6,394,092 B1
(45) Date of Patent: May 28, 2002

(54) FASTENING STRUCTURE ADAPTED FOR BOTH TRACHEAL AND ENDO-TRACHEAL USE

(76) Inventors: Kimberly L. Barrett, 3012 W. Fairview Ave., Spokane, WA (US) 99205; Jessica A. Krzyzanek, 1018 E. Glass, Spokane, WA (US) 99207; Jeff Bendio, 13903 E. Sprague #8, Spokane, WA (US) 99216

( * ) Notice: Subject to any disclaimer, the term of this patent is extended or adjusted under 35 U.S.C. 154(b) by 0 days.

(21) Appl. No.: 09/497,262

(22) Filed: Feb. 3, 2000

(51) Int. Cl.[7] .............................................. A61M 16/00
(52) U.S. Cl. ................................... 128/207.17; 128/912
(58) Field of Search ..................... 128/207.14, 207.15, 128/207.17, 207.29, 912, DIG. 26, 200.26

(56) References Cited

U.S. PATENT DOCUMENTS

| | | | | |
|---|---|---|---|---|
| 3,486,730 A | | 12/1969 | Potash ...................... 251/149.7 |
| 3,760,811 A | * | 9/1973 | Andrew ....................... 128/351 |
| 3,973,569 A | * | 8/1976 | Sheridan et al. ............ 128/351 |
| 4,193,174 A | * | 3/1980 | Stephens ..................... 24/249 |
| 4,249,529 A | * | 2/1981 | Nestor et al. .......... 128/207.17 |
| 4,351,331 A | * | 9/1982 | Gereg ................... 128/207.17 |
| 4,449,524 A | | 5/1984 | Gray .................... 128/202.27 |
| 4,498,903 A | * | 2/1985 | Mathew ...................... 604/174 |
| 4,516,293 A | * | 5/1985 | Beran ................... 128/207.17 |
| 4,774,944 A | * | 10/1988 | Mischinski ............ 128/207.17 |
| 4,832,019 A | * | 5/1989 | Weinstein et al. ...... 128/207.17 |
| 4,846,167 A | | 7/1989 | Tibbals .................. 128/202.27 |
| 4,852,563 A | | 8/1989 | Gross .................... 128/202.27 |
| 5,026,352 A | * | 6/1991 | Anderson ................... 604/178 |
| 5,176,415 A | | 1/1993 | Choksi ........................ 285/331 |
| 5,282,463 A | * | 2/1994 | Hammersley .......... 128/207.15 |
| 5,295,480 A | * | 3/1994 | Zemo .................... 128/207.17 |
| 5,305,742 A | * | 4/1994 | Styers et al. ........... 128/207.17 |
| 5,320,097 A | * | 6/1994 | Clemens et al. ....... 128/207.17 |
| 5,343,857 A | | 9/1994 | Schneider et al. ...... 128/202.27 |
| 5,345,931 A | * | 9/1994 | Battaglia, Jr. et al. .. 128/207.17 |
| 5,419,319 A | * | 5/1995 | Werner .................. 128/207.17 |
| 5,437,273 A | * | 8/1995 | Bates et al. ............ 128/207.17 |
| 5,513,633 A | * | 5/1996 | Islava .................... 128/207.17 |
| 5,551,421 A | * | 9/1996 | Noureldin et al. ...... 128/207.17 |
| 5,782,236 A | * | 7/1998 | Ess ........................ 128/207.17 |
| 5,806,516 A | * | 9/1998 | Beattie .................. 128/207.17 |
| 5,829,430 A | * | 11/1998 | Islava .................... 128/200.26 |
| 6,009,872 A | * | 1/2000 | Delaplane et al. ...... 128/207.17 |
| 6,029,668 A | * | 2/2000 | Freed .................... 128/207.17 |
| 6,047,699 A | * | 4/2000 | Ryatt et al. ............ 128/207.17 |
| 6,050,263 A | * | 4/2000 | Choksi et al. .......... 128/207.14 |
| 6,067,985 A | * | 5/2000 | Islava .................... 128/207.17 |
| 6,105,573 A | * | 8/2000 | Delaplane et al. ...... 128/200.26 |

\* cited by examiner

*Primary Examiner*—John G. Weiss
*Assistant Examiner*—Teena Mitchell
(74) *Attorney, Agent, or Firm*—David S. Thompson

(57) ABSTRACT

A fastening structure is adapted for use with both tracheal and endo-tracheal assisted breathing device. The fastening structure provides a fastening ring and a fastening bracket. The fastening structures are adapted for connection to prior art assisted breathing components currently adopted in most medical facilities. In an endo-tracheal application, where the endo-tracheal tube passes through the patient's mouth, first and second fastening rings are attached to the auxiliary port and to the ventilator attachment port, respectively, of the ventilator adaptor. The U-shaped opening of a fastening bracket is passed over the endo-tracheal adapter which is attached to the ventilation adapter. First and second legs, extending from the fastening bracket, lock onto the first and second rings. The connection between the fastening bracket and the fastening rings prevents unwanted separation between the endo-tracheal adapter and the ventilation adapter. In a tracheal application, a single fastening ring is carried by the tracheal adapter and is secured by tracheal ties which encircle the neck of the patient. In this application, the fastening ring prevents unwanted separation between the tracheal adapter and the tracheal tube.

2 Claims, 7 Drawing Sheets

FASTENING STRUCTURE ADAPTED FOR BOTH TRACHEAL AND ENDO-TRACHEAL USE

CROSS-REFERENCES

There are no applications related to this application filed in this or any foreign country.

BACKGROUND

Patients with breathing problems may be assisted in the breathing process by a ventilator system. Unfortunately, due to the multi-component design from which the most widely used assisted breathing apparatus is assembled, a serious hazard exists due to the tendency of certain components to separate.

Ventilator systems include tracheal and endo-tracheal types. Endo-tracheal tubes pass through the patient's mouth, while tracheal tubes pass through a hole made in the patient's trachea. Generally, tracheal tubes assist patients who have longer-term breathing problems, while an endo-tracheal tube passing through the patient's mouth is used to assist patients with shorter-term breathing problems.

Referring to the prior art view of FIG. 1, an exploded view of the prior art endo24 tracheal apparatus is seen. This apparatus includes a central ventilator adapter 100, which is attached to a ventilator attachment 120 having both in and out vents, a suction port 140 and suction adapter 150, and a cap 160 for terminating a dead end or auxiliary port on the central ventilator adapter. An endo-tracheal adapter 180, extending from the endo-tracheal tube 200, is also attached to the central ventilator adaptor 100. The endo-tracheal tube is then positioned within the patient's trachea, where it provides breathing assistance.

A serious hazard exists for patients using endo-tracheal tubes to assist in the breathing process. Unfortunately, it is common for the endo-tracheal adapter 180 to separate, or "pop off," from the central ventilator adapter 100. This is because this fitting is of the friction-fit type, and requires little force to cause it to fail. In the event of failure, the patent is unable to breathe, and will require immediate medical assistance in reassembling the tubes.

This safety issue is a difficult one for which to find a solution. In particular, the central ventilator adapter and related components have been adopted in an overwhelming and widespread manner. Additionally, there is general satisfaction overall with this apparatus, despite the safety issue disclosed above. Therefore, it is unlikely that an improved substitute could achieve commercial success, and therefore it is unlikely that an improved substitute could result in the saving of lives. Prior art solutions to the problem of tube separation have utilized different structures, and would therefore be unlikely to achieve commercial or medical success.

A similar serious safety hazard exists for patients using tracheal tubes to assist in the breathing process. Where the patient requires long-term care, a tracheal tube 300 is inserted into the patient's trachea. In this circumstance, a tracheal adapter 350 is attached to both the ventilator attachment 120 and to the tracheal tube 300. It is unfortunately the case that the tracheal tube will frequently separate from the ventilator attachment. This is because this fitting is of the friction-fit type, and requires little force to cause it to fail. In the event of failure, the patent is unable to breathe, and will require immediate medical assistance in reassembling the tubes.

This safety issue is also a difficult one for which to find a solution. In particular, the tracheal adapter 350 has been adopted in an overwhelming and widespread manner. Additionally, there is general satisfaction overall with this apparatus, despite the safety issue disclosed above. Therefore, it is unlikely that an improved substitute could achieve commercial success, and therefore it is unlikely that an improved substitute could result in the saving of lives. Prior art solutions to the problem of tube separation have utilized different structures, and would therefore be unlikely to achieve commercial or medial success.

What is needed is a safety device which could be used in conjunction with the widely used components associated with assisted breathing in both endo-tracheal and tracheal applications. The safety device should not require medical facilities to discontinue purchases of the current components, but should instead be adapted to work with components that have already been commercially adopted in a widespread manner. The safety device should also be adapted for use with both tracheal and endo-tracheal applications.

SUMMARY

The present invention is directed to an apparatus that satisfies the above needs. A novel safety device adapted for both tracheal and endo-tracheal use is disclosed that is adapted for use in conjunction with an industry standard central ventilator adapter, ventilator attachment and related components. The safety device does not require medical facilities to discontinue purchases of the current components, but instead is adapted to work with components that have already been adopted in a widespread manner.

In a tracheal application, a tracheal tube 300 extends from the patient's trachea, passes through a fastening plate 330, and attaches to a tracheal adapter 350. The tracheal adapter in turn attaches to a ventilator attachment 120, which which supplies and removes air. A middle portion of a tracheal tie 320 extends behind the patient's neck, while the ends of the tracheal ties typically pass through holes defined in the fastening plate and then fold back against themselves where they are attached by VELCRO® or similar fastener, thereby preventing the unwanted movement of the tracheal tube. Due to the nature of the mechanical fit of the various components described, and their frictional attachment to one another, there is a connection 340 prone to accidental separation between the tracheal tube 300 and the tracheal adapter 350.

To prevent this separation, the end of the tracheal adapter 350 most distant from the patient is passed through the tube passage 25 defined within a fastening ring 20. The ends of the tracheal ties 320, which are ordinarily attached through the fastening plate, are extended to pass through tie passages 29 defined in diametrically opposed blunt end portions 22 of the fastening ring. The ends of the tracheal ties are then folded back against themselves for fastening with VEL-CRO® or similar fastener. Unwanted movement of the tracheal tube is thereby prevented, as in the prior art, but additionally the tracheal adapter 350 is held in place with respect to the tracheal tube 300, preventing unwanted separation between the two.

In an endo-tracheal application, a ventilation adapter 100 supports a ventilator attachment 120, which supplies and removes air. The ventilation adapter also connects to an endo-tracheal adapter 180, which in turn connects to an endo-tracheal tube. Due to the nature of the mechanical fit of the various components described, and their frictional attachment to one another, there is a connection 220 prone to accidental separation between the endo-tracheal adapter 180 and the ventilation adapter 100.

To prevent this separation, the auxiliary port 102 and the ventilator attachment port 104 of the ventilation adapter 100 are each inserted into the tube passage 25 defined within first and second fastening rings 20. Each fastening ring is oriented so that the inner surfaces face the ventilation adapter 100.

A fastening bracket 60 attaches to both fastening rings, holding the assisted breathing components together. The U-shaped opening 62 defined in the body 61 of a fastening bracket 60 is carried about the endo-tracheal adapter 180. The pair of elongated legs 65 extending from the body pass through the fastener passages 27 defined in one of the blunt ends, in each of the first and second fastening rings, and connect by snapping against the lock support surface 28 of each ring.

It is therefore a primary advantage of the present invention to provide a novel fastening structure which prevents the unwanted separation of ventilation tubes in both a tracheal and an endo-tracheal assisted breathing application.

Another advantage of the present invention is to provide a novel fastening structure which is adapted for use with tracheal and endo-tracheal components which are currently universally used, and which does not require substitution of any components.

A still further advantage of the present invention is to provide a novel fastening structure which prevents the unwanted separation of ventilation tubes that is easily and quickly attached to universally used assisted breathing components, even during times where the patient requires immediate assistance, and where time is of the essence.

Other objectives, advantages and novel features of the invention will become apparent to those skilled in the art upon examination of the specification and the accompanying drawings.

DRAWINGS

These and other features, aspects, and advantages of the present invention will become better understood with regard to the following description, appended claims, and accompanying drawings where:

FIG. 1, Prior Art, is an exploded orthographic view of the prior art endo-tracheal assisted breathing apparatus with which the instant invention is adapted for use.

DESCRIPTION

Figure 1:
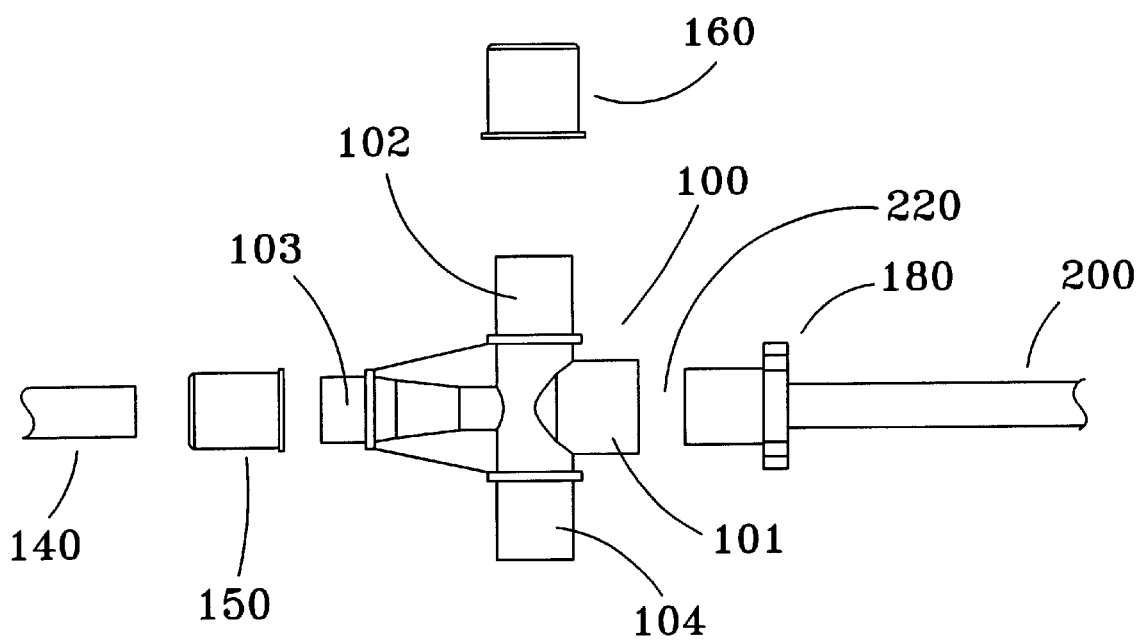
Figure 1:
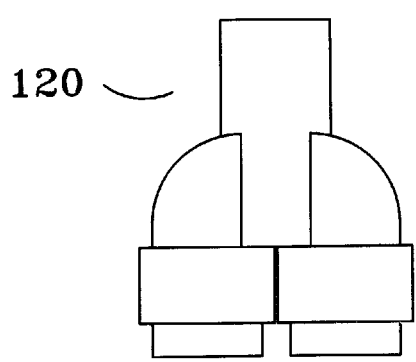

Referring generally to FIGS. 2 through 7, a version of the fastening structure of the invention adapted for use with both tracheal and endo-tracheal assisted breathing devices is seen. The fastening structure provides a fastening ring 20 and a fastening bracket 60. The fastening structures are adapted for connection to prior art assisted breathing components currently adopted in most medical facilities. In an endo-tracheal application, where the endo-tracheal tube 200 passes through the patient's mouth, first and second fastening rings 20 are attached to the auxiliary port and to the ventilator attachment port, respectively, of the ventilator adaptor 100. The U-shaped opening of a fastening bracket 60 is passed over the endo-tracheal adapter 180 which is attached to the ventilation adapter. First and second elongate legs, extending from the fastening bracket, lock onto the first and second rings. The connection between the fastening bracket and the fastening rings prevents unwanted separation between the endo-tracheal adapter and the ventilation adapter. In a tracheal application, a single fastening ring 20 is carried by the tracheal adapter 350 and is secured by tracheal ties 320 extending behind the neck of the patient. In this application, the fastening ring 20 prevents unwanted separation between the tracheal adapter 350 and the tracheal tube 300.

As seen particularly in FIGS. 1–4, a ventilation adapter 100 is well-known in the prior art, and has been generally adopted for use in endo-tracheal assisted breathing applications. The ventilation adapter provides an endo-tracheal connector port 101 which is sized for attachment to the endo-tracheal adapter 180. The endo-tracheal connector port 101 is prone to unwanted separation with the endo-tracheal adapter 180. The ventilator adapter 100 also provides an auxiliary port 102, which is typically closed by a cap 160. A suction port 103 is opposite the endo-tracheal connector. The suction port 103 is typically attached to a suction adapter 150 and to a suction port 140 which is used to provide suction, if needed, to clear unwanted debris. A ventilator attachment port 104 is opposite the auxiliary port, and allows attachment to the ventilator attachment 120.

A connection tube 123, extending from the ventilator attachment 120, is friction-fit to the ventilator attachment port 104 of the ventilation adapter 100. Air input and air output tubes 121, 122 provide and remove the air breathed by the patient.

Continuing to refer to FIGS. 1–4, an endo-tracheal adapter 180 is carried by a first end of the endo-tracheal tube 200. The endo-tracheal adapter is connected to the endo-tracheal connector port 101 of the ventilation adapter 100. The second end of the endo-tracheal tube 200 passes through the patient's mouth and into the trachea.

As seen in FIG. 1, the endo-tracheal adapter 180 is factory sealed to the endo-tracheal tube 200. At the opposite end of the endo-tracheal adapter 180, a ventilation adapter connection tube 181 is sized for a friction-fit connection to the endo-tracheal connector port 101. An annular plate 182 typically defines a plurality of sockets 183.

Figure 2:
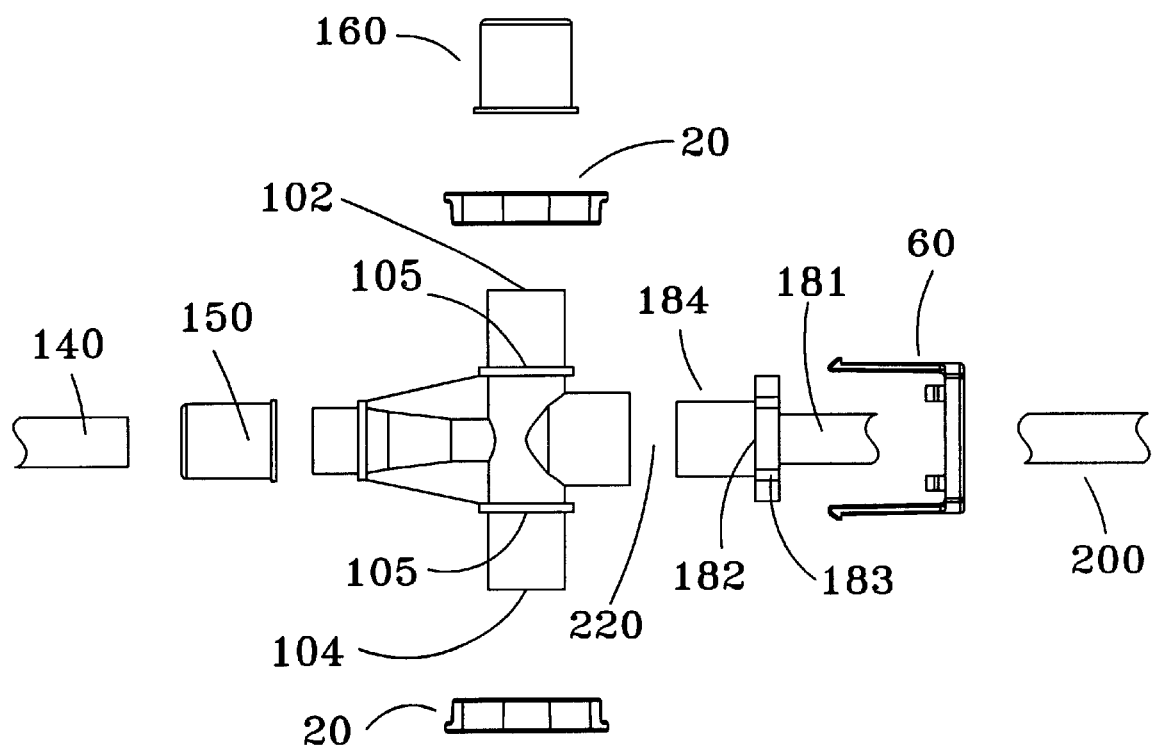
FIG. 2 is an exploded orthographic view, similar to that of FIG. 1, illustrating a version of the fastening ring and fastening bracket of the invention.
Figure 2:
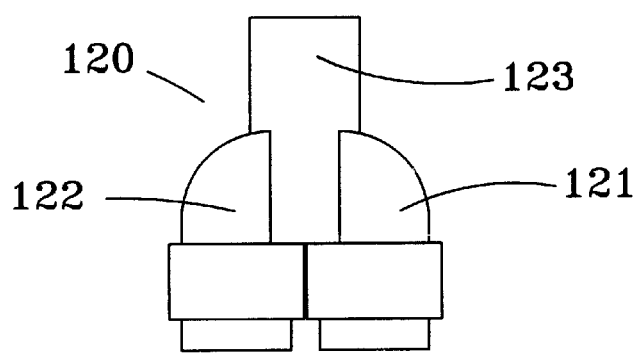

Referring to FIGS. 1 and 2, the area of unwanted separation 220 is seen. Due to the construction of the prior art assisted breathing apparatus, there is a tendency for the endo-tracheal connection port 101 of the ventilation adapter 100 to separate from the endo-tracheal adapter 180 at location 220.

Figure 7:
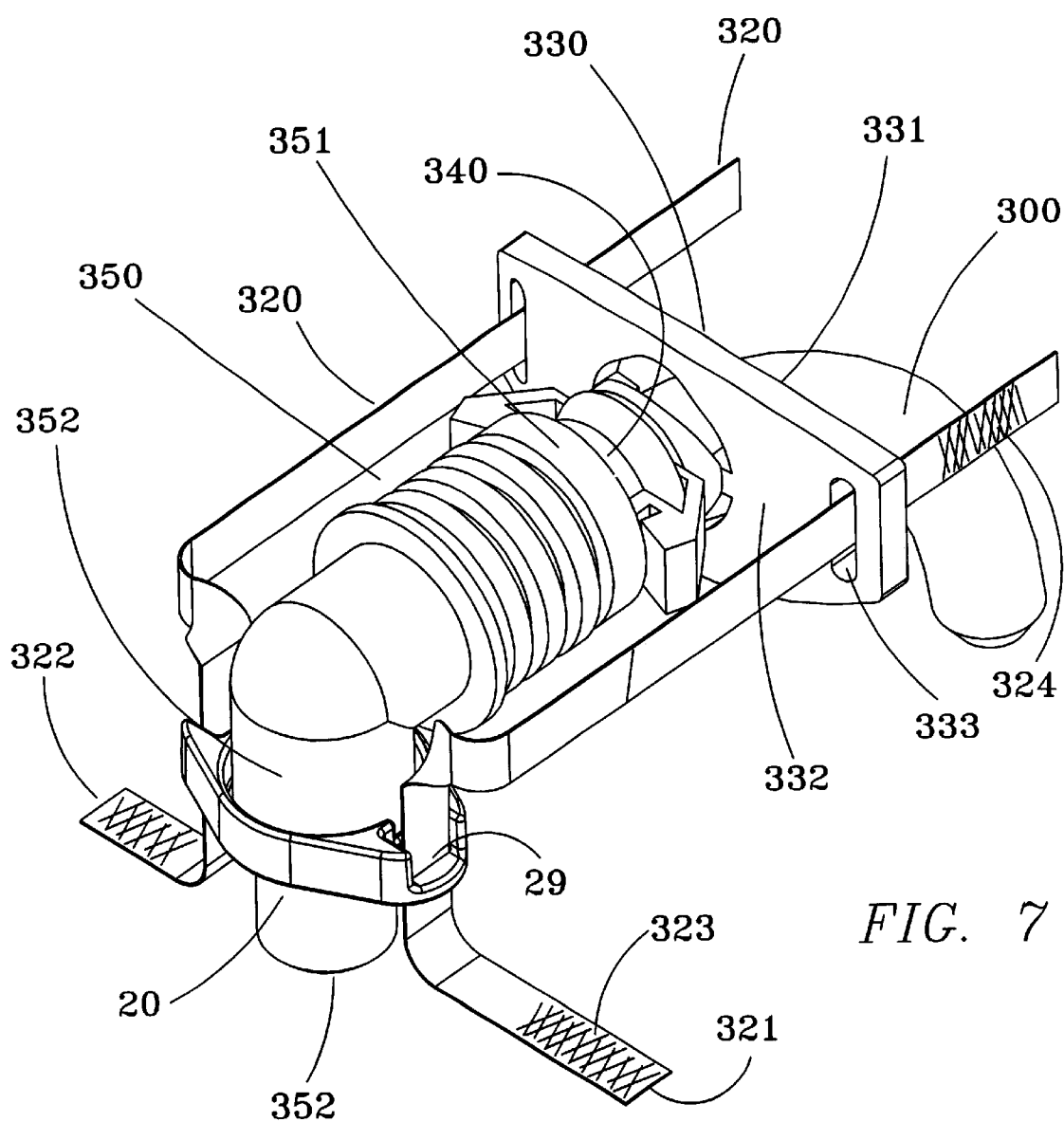
FIG. 7 is a perspective view the fastening ring of FIGS. 5A and 5B securing an assisted breathing tracheal apparatus.

Referring to FIG. 7, a tracheal adapter 350 is seen. Such an adapter is known in the prior art and widely adopted by medical facilities for use by patient's needing longer term breathing assistance. An outer end 351 is attached to the tracheal tube 300, which is inserted into the patient's trachea. An inner end 352 is attached to the connection tube 123 of the ventilator attachment 120.

A fastening plate 330 is used by the prior art to maintain the position of the tracheal tube 300. An inner surface 331 of the fastening plate is carried against the patient's throat, while an outer surface 332 faces the tracheal adapter 350. Tracheal tie passage holes 333 allow a tracheal tie strap 320 to be fastened through the fastening plate. The tracheal tie passes behind the patient's neck, while the ends pass through the holes 333 and are folded back against themselves. VELCRO® or similar hook and loop fastener secures the ends of the tracheal tie.

Referring to FIG. 7, the area of unwanted separation 340 is seen. Due to the construction of the prior art assisted breathing apparatus, there is a tendency for the tracheal tube 300 to separate from the tracheal adapter 350 at location 340.

Figure 5A:
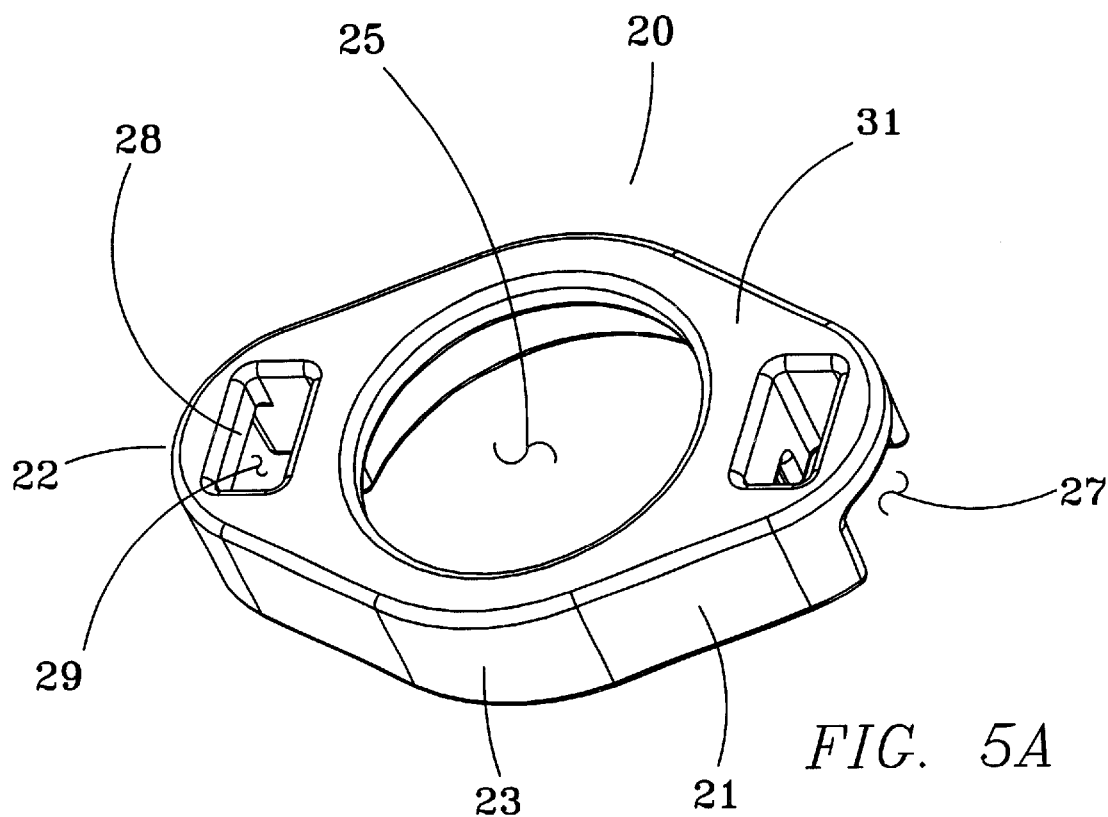
FIGS. 5A and 5B are somewhat enlarged perspective views of a version of the fastening ring.
Figure 5B:
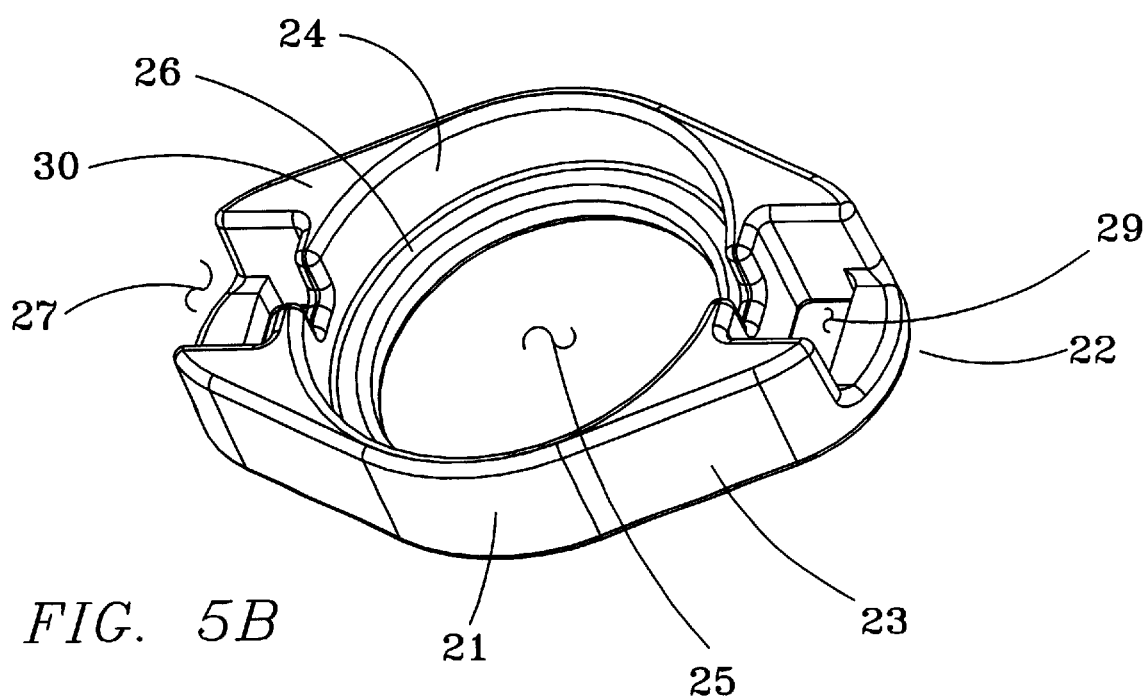

Referring particularly to FIGS. 5A and 5B, the construction of a preferred version of the fastening ring 20 is seen. In the endo-tracheal application seen in the exploded and assembled views of FIGS. 2 and 3, the fastening ring is sized to fit over the auxiliary and ventilator attachment ports 102, 104. In the tracheal application seen in the perspective view of FIG. 7, the same fastening ring fits over the inner end 352 of the tracheal adapter 350.

The fastening ring includes a disk-shaped body having generally oval outer sidewall 23, with two opposed curving sides 21 connected to two opposed blunt ends 22. A circular tube passage 25 is defined between the inner and outer surfaces 30, 31, and is sized to fit over the ventilator attachment port 104 and the auxiliary port 102 of the ventilator adapter 100 and the inner end 352 of the tracheal adapter 350.

A shoulder 26, best seen in FIG. 5B, has a diameter that is slightly less than the inner sidewall 24. In the endo-tracheal application, the shoulder 26 seats against the stop 105 defined on the auxiliary port 102 and ventilator attachment port 104 of the ventilation adapter 100. In the tracheal application, the shoulder 26 seats against the inner end 351 of the tracheal adapter 350.

Figure 4:
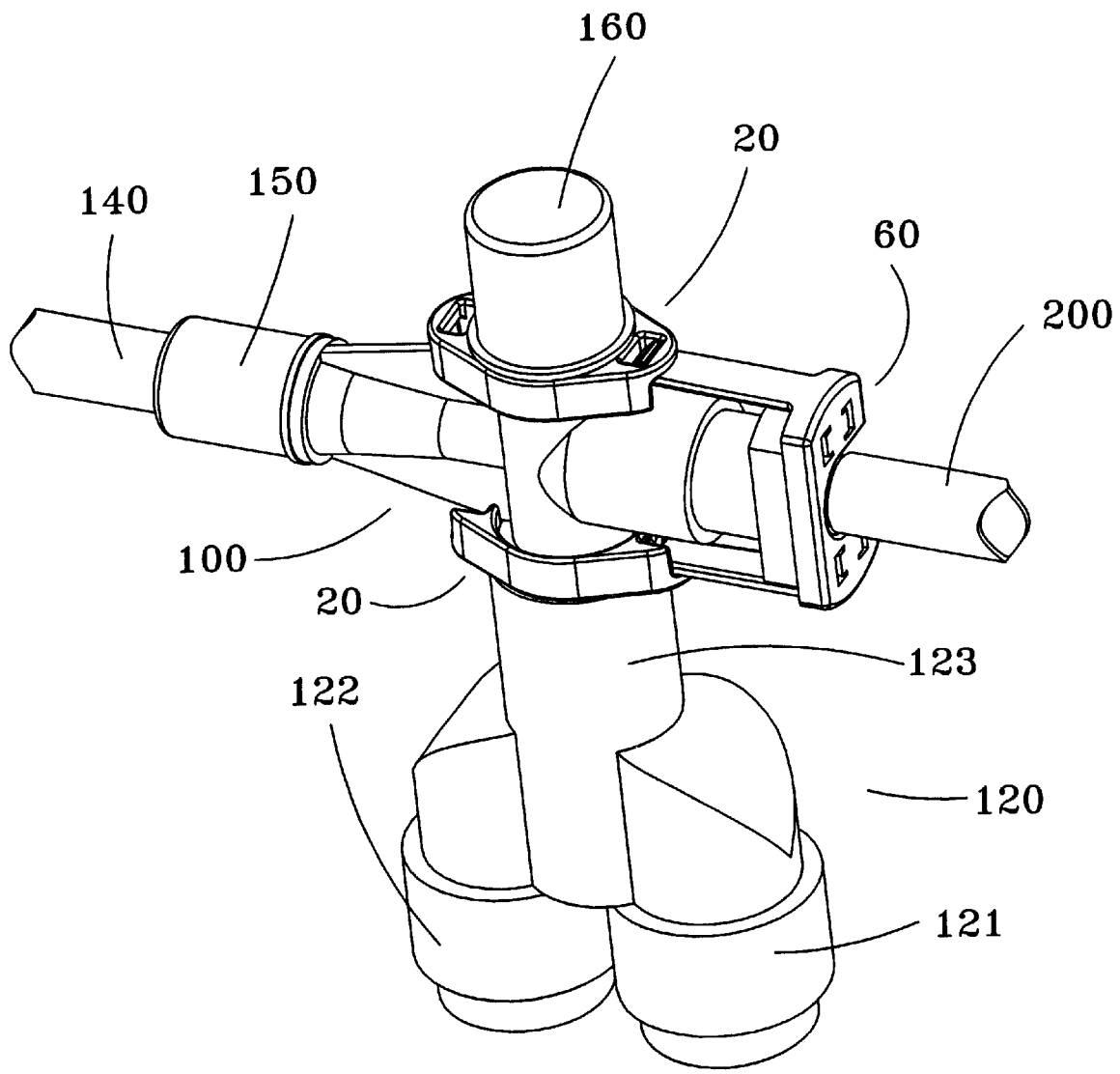
FIG. 4 is a perspective view of the assembled parts, similar to that of FIG. 3.

As is best seen in FIGS. 4, 5 and 6, a fastener passage 27 and lock support surface 28 are sized to allow the elongated legs 65 and hooks 66 of the fastening bracket 60 to connect to the fastening ring 20. The fastener passage 27 is defined in the outer sidewall of the blunt end 22 of the fastening ring, allowing the elongated leg 65 to be inserted into the fastener passage, while the hook 66 passes partly through the tie passage 29, and is supported by the lock support surface 28.

Referring particularly to FIGS. 5 and 7, it can be seen that the outer sidewall adjacent to the first and second blunt ends defines first and second tie passages 29. The tie passages adapt the fastening ring for attachment to the tracheal ties used by the prior art to secure the tracheal tube 300. A tracheal ties is a narrow strap that passes behind the neck of the patient. In the prior art application, first and second ends of the tracheal tie attach to the holes 333 defined in the fastening plate. In the present invention, the first and second ends 321, 322 of a tracheal tie 320 pass through first and second holes 333 defined in the fastening plate 330, and then through the first and second tie passages 29. Having passed through the first and second tie passages, the first and second ends are then folded back against themselves, allowing sections of male VELCRO® 323 and female VELCRO® 324 or similar hook and loop fastener to mate.

As seen in FIGS. 2, 3, 4 and 6, a fastening bracket 60 is attachable to first and second fastening rings. The fastening bracket is adapted for use where the assisted breathing apparatus is of the endo-tracheal type, seen in the assembled form in FIG. 4. By wrapping the U-shaped opening 62 about the endo-tracheal adapter 180 and attaching the elongated legs 65 to first and second fastening rings supported by the ventilation adapter 100, the fastening bracket 60 prevents separation between the ventilation adapter 100 and the endo-tracheal adapter 180 at location 220.

Figure 6A:
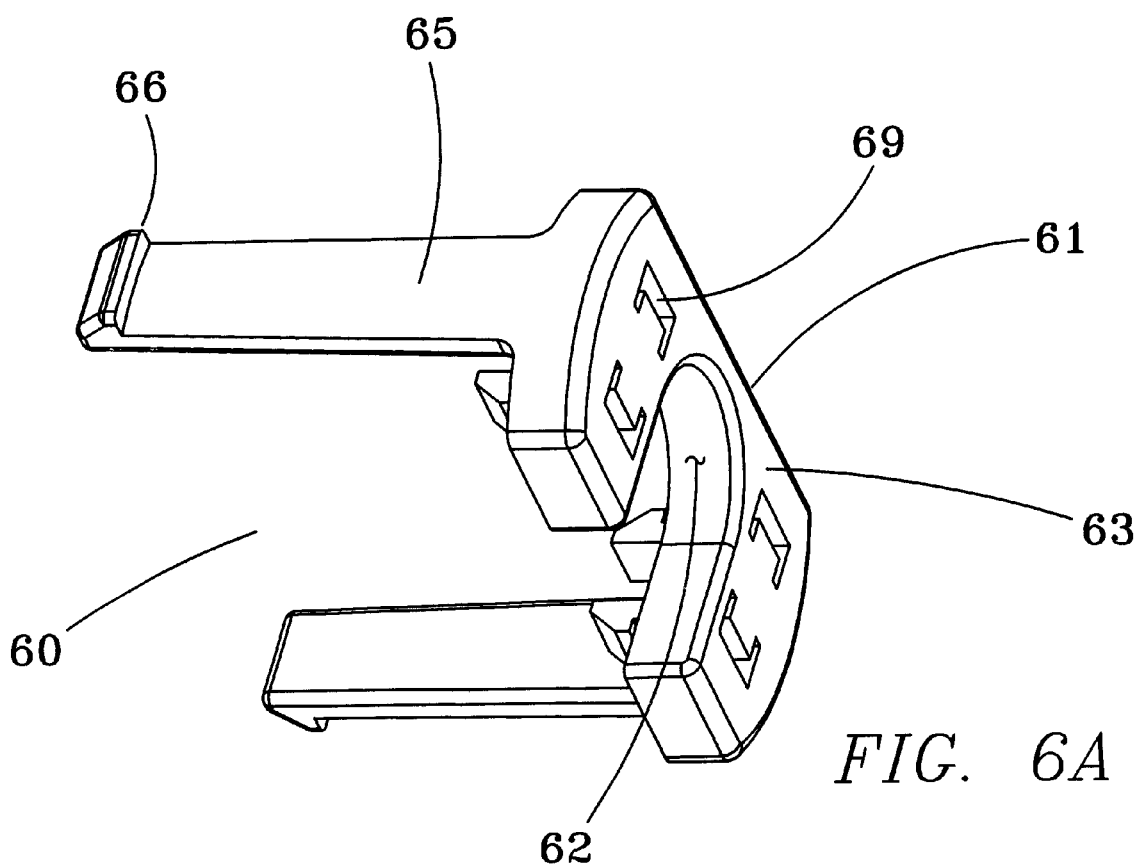
FIGS. 6A and 6B are somewhat enlarged perspective views of a version of the fastening bracket.
Figure 6B:
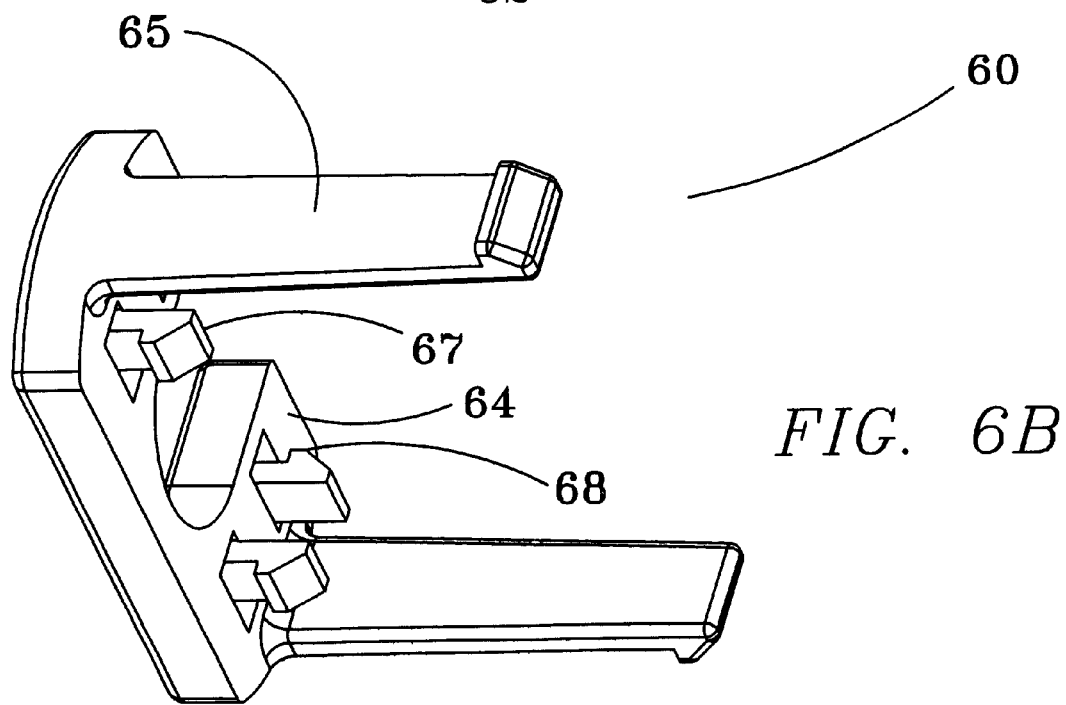

Referring particularly to FIGS. 6A and 6B, the construction of a preferred version of the fastening bracket may be understood. A body 61 having top and bottom surfaces 63, 64 defines a U-shaped opening 62 which is sized to wrap about the endo-tracheal tube 200 adjacent to the annular plate 182 of the endo-tracheal adapter 180. Due to the U-shaped construction, the fastening bracket 60 may be rapidly attached to the endo-tracheal adapter after endo-tracheal adapter 180 and ventilation adapter 100 have been assembled and are operating to assist the breathing of the patient.

First and second elongated legs 65 extend from the bottom surface 64 of the body 61. The elongated legs are sized to pass through the fastener passages 27 defined in the outer sidewall 23 of the blunt end 22 of a fastening ring. The end of each leg supports a hook 66, which is sized to attach to the lock support surface 28 of a fastening ring 20, as seen in FIG. 4.

Referring again to FIG. 6, four short legs 67, each having a hook 68, extend from the bottom surface 64 of the body 61. Openings 69 near the short legs facilitate the manufacturing process. The short legs extend into openings or sockets 183 defined in the annular plate 182 of the endo-tracheal adapter 180. The short legs reinforce the connection and alignment of the bracket 60 with respect to the endo-tracheal adapter 180. In particular, the short legs prevent unwanted rotation and separation.

Figure 3:
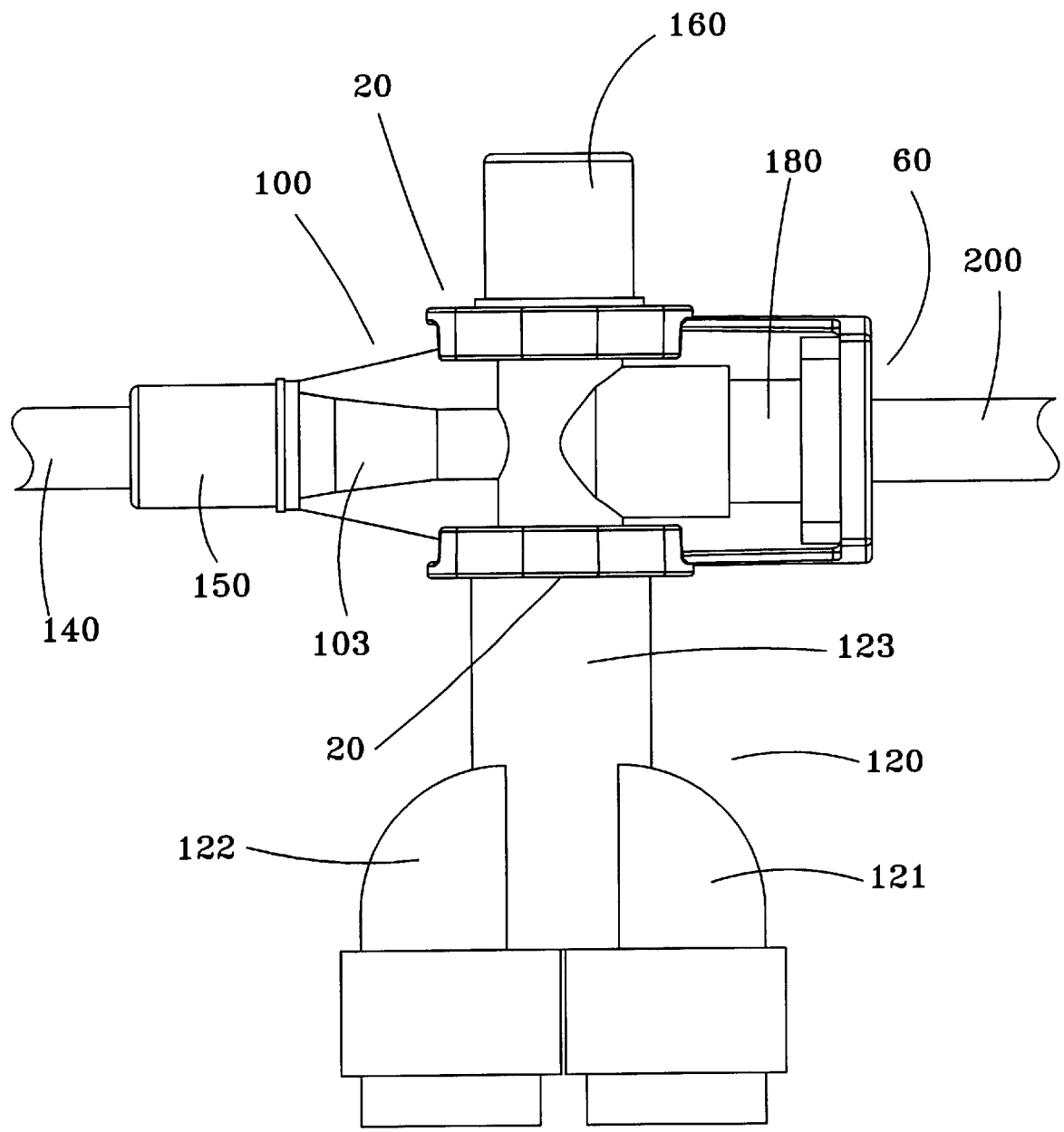
FIG. 3 is a view, similar to that of FIG. 2, showing the parts in an assembled form.

To use the fastening ring 20 and fastening bracket 60 in an endo-tracheal assisted breathing application, as seen in FIGS. 2–4, medical personnel pass first and second fastening rings over the auxiliary port 102 and ventilator attachment port 104 of the ventilator adaptor. The inner surfaces 30 are directed toward the center of the ventilation adapter, so that the shoulder 26 seats against the top 105.

The U-shaped opening 62 of the fastening bracket 60 is then passed over the endo-tracheal tube 200 adjacent to the annular plate 182 of the ventilator attachment 180. The first and second elongated legs 65 inserted into the fastener passages 27 of the first and second fastening rings. The hook 66 of each elongated leg 65 snaps into place on the lock support surface 28 of each fastening ring 20. Similarly, the short legs 67 and hooks 68 snap into the sockets 183 defined in the endo-tracheal adapter 180.

To use the fastening ring 20 in a tracheal assisted breathing application as seen in FIG. 7, a fastening ring is passed over the inner end 352 of the tracheal adapter 350, and the tracheal assisted breathing apparatus is assembled as usual. The first and second ends 321, 322 of the tracheal ties 320 are passed through the first and second holes 333 defined in the fastening plate 330, and then through the first and second tie passages 29 in the fastening ring 20, respectively. The ends of the tracheal tie are then folded back against themselves, allowing the male VELCRO® 323 to adhere to the female VELCRO® 324. Because the fastening ring is held in place by the tracheal tie, and is secured to the tracheal adapter 350, the tracheal adapter will not separate from the tracheal tube 300 at location 340.

The previously described versions of the present invention have many advantages, including a primary advantage of providing a novel fastening structure which prevents the unwanted separation of ventilation tubes in both a tracheal and an endo-tracheal assisted breathing application.

Another advantage of the present invention is to provide a novel fastening structure which is adapted for use with tracheal and endo-tracheal components which are currently universally used, and which does not require substitution of any components.

A still further advantage of the present invention is to provide a novel fastening structure which prevents the unwanted separation of ventilation tubes that is easily and quickly attached to universally used assisted breathing components, even during times where the patient requires immediate assistance, and where time is of the essence.

Although the present invention has been described in considerable detail and with reference to certain preferred versions, other versions are possible. For example, while a fastening structure including a hook 66 carried by the elongated leg 65 which snaps against the lock support surface 28 is disclosed, alternative fastening or locking structures could be substituted. Therefore, the spirit and scope of the appended claims should not be limited to the description of the preferred versions disclosed.

In compliance with the U.S. Patent Laws, the invention has been described in language more or less specific as to methodical features. The invention is not, however, limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A fastener for attachment to an assisted breathing apparatus, the fastener comprising:
    (A) a first fastening ring, comprising:
        (a) a disk-shaped body having generally oval outer sidewall with first and second opposed curving sides connected to first and second opposed blunt ends;
        (b) wherein the disk-shaped body defines a circular tube passage between an inner and an outer surface of the disk-shaped body;
        (c) wherein the first and second blunt ends define first and second tie passages;
        (d) first and second lock support surfaces adjacent to the first and second tie passages, respectively; and
        (e) wherein the outer sidewall adjacent to the first and second blunt ends defines first and second fastener passages, respectively;
    (B) a second fastening ring, comprising:
        (a) a disk-shaped body having generally oval outer sidewall with first and second opposed curving sides connected to first and second opposed blunt ends;
        (b) wherein the disk-shaped body defines a circular tube passage between an inner and an outer surface of the disk-shaped body;
        (c) wherein the first and second blunt ends define first and second tie passages;
        (d) first and second lock support surfaces adjacent to the first and second tie passages, respectively; and
        (e) wherein the outer sidewall adjacent to the first and second blunt ends defines first and second fastener passages, respectively; and
    (C) a fastening bracket, comprising:
        (a) a body defining a U-shaped opening;
        (b) first and second elongated legs, extending from the body and passing through the first and second fastener passages, respectively; and
        (c) first and second hooks, extending from the first and second elongated legs, respectively, and retained by the lock support surface of the first and second fastening rings, respectively.

2. The fastener of claim 1, wherein the fastening bracket additionally comprises at least one short leg, carried by the body and oriented in the same direction as the first and second elongated legs.

* * * * *